United States Patent [19]
Rodriguez et al.

[11] Patent Number: 6,149,921
[45] Date of Patent: Nov. 21, 2000

[54] VACCINE COMPOSITIONS FOR ELICITING AN IMMUNE RESPONSE AGAINST N-ACETYLATED GANGLIOSIDES AND THEIR USE FOR CANCER TREATMENT

[75] Inventors: Rolando Perez Rodriguez; Luis Enrique Fernandéz Molina; Gilda Marquina Rodriguéz; Adriana Carr Pérez; Oscar Gonzalo Valiente Hernandéz, all of Habana, Cuba

[73] Assignee: Centro de Inmunologia Molecular, Habana, Cuba

[21] Appl. No.: 09/061,710

[22] Filed: Apr. 17, 1998

Related U.S. Application Data

[63] Continuation-in-part of application No. 08/365,684, Dec. 29, 1994, Pat. No. 5,788,985.

[30] Foreign Application Priority Data

Nov. 10, 1997 [CU] Cuba ......................................... 130/97

[51] Int. Cl.$^7$ .................................................. A61K 39/00
[52] U.S. Cl. .................................... 424/277.1; 424/184.1; 424/137.1; 424/422; 424/423; 424/283.1; 424/278.1; 424/194.1; 424/234.1; 424/141.1; 424/155.1; 424/156.1; 424/174.1; 530/387.5; 530/389.7; 530/395; 530/806; 530/828; 530/387.7; 530/388.1; 514/42; 514/25; 514/885
[58] Field of Search .............................. 424/184.1, 277.1, 424/137.1, 422, 423, 283.1, 278.1, 194.1, 234.1, 141.1, 155.1, 156.1, 174.1; 514/42, 25, 885; 530/387.5, 389.7, 393, 387.1, 388.1; 436/813

[56] References Cited

U.S. PATENT DOCUMENTS

| | | | |
|---|---|---|---|
| 4,950,750 | 8/1990 | Ogawa et al. | 536/18.7 |
| 5,026,557 | 6/1991 | Estis et al. | |
| 5,102,663 | 4/1992 | Livingston et al. | |
| 5,449,610 | 9/1995 | Lillehoj | |
| 5,591,772 | 1/1997 | Lane et al. | |
| 5,788,985 | 8/1998 | Rodriguez et al. | |

FOREIGN PATENT DOCUMENTS

| | | |
|---|---|---|
| 0 280 209 A2 | 8/1988 | European Pat. Off. |
| 0 586 002 A2 | 3/1994 | European Pat. Off. |
| 0661061 | 7/1995 | European Pat. Off. |
| WO 87/06840 | 11/1987 | WIPO |
| WO 90/14104 | 11/1990 | WIPO |

OTHER PUBLICATIONS

Dohi et al., "An IgG$_3$ Monoclonal Antibody Established after Immunization with G$_{M3}$ Lactone:Immunochemical Specificity and Inhibition of Melanoma Cell Growth in Vitro and in Vivo", *Cancer Research*, vol. 48, pp. 5680–5685, 1988.

Furukawa et al., "Analysis of the Expression of N–Glycolylneuraminic Acid–containing Gangliosides in Cells and Tissue using Two Human Monoclonal Antibodies", *The Journal of Biological Chemistry*, vol. 263, No. 34, pp. 18507–18512, 1988.

Hamiltion et al., "Ganglioside Expression On Human Malignant Melanoma Assessed By Quantitative Immune Thin–Layer Chromatography", *Int. J. Cancer*, 53, pp. 566–573, 1993.

Helling et al., "G$_{M2}$–KLH Conjugate Vaccine: Increased Immunogenicity in Melanoma Patients After Administration With Immunological Adjuvant QS–21", *Cancer Research* 55, pp. 2783–2788, Jul. 1, 1995.

Livingston et al., "Characterization of IgG and IgM Antibodies Induced in Melanoma Patients by Immunization with Purified G$_{M2}$ Ganglioside", *Cancer Research* 49, pp. 7045–7050, Dec. 15, 1989.

Livingston et al., "GD3/proteosome vaccines induce consistent IgM antibodies against the ganglioside GD3", *Vaccine*, vol. 11, Issue 12, pp. 1199–1204, 1993.

Portoukalian et al., "Humoral Immune Response in Disease–Free Advanced Melanoma Patients After Vaccination with Melanoma–Associated Gangliosides", *International Journal of Cancer* 49, pp. 893–899, 1991.

Vogel F.R. and M.F. Powell. Compendium of Vaccine Adjuvants and Excipients. Plenum Publishing Corporation. New York, NY. 1994 ;p. 47, 1994.

Livingston et al, Cancer Research 49:7045–7050, 1989.

Carlsson et al., "Protein Thiolation and Reversible Protein–Protein Conjugation", *Biochem. J.*, 173, pp. 723–737, 1978.

Hakomori et al., "Isolation and Characterization of Glycosphingolipid from Animal Cells and Their Membranes", *Methods in Enzymology*, vol. 32, pp. 345–367, 1974.

Helling et al., "G$_{D3}$ Vaccines for Melanoma: Superior Immunogenicity of Keyhole Limpet Hemocyanin Conjugate Vaccines", *Cancer Research* 54, pp. 197–203, Jan. 1, 1994.

Livingston et al., "Approaches to Augmenting the IgG Antibody Response to Melanoma Ganglioside Vaccines", *Annals New York Academy of Sciences*, pp. 204–213.

Livingston, Philip O., "Approaches to Augmenting the Immunogenicity of Melanoma Gangliosides: From Whole Melanoma Cells to Ganglioside–KLH Conjugate Vaccines", *Immunological Reviews*, No. 145, pp. 147–166, 1995.

(List continued on next page.)

*Primary Examiner*—Donna C. Wortman
*Assistant Examiner*—Robert A. Zemar
*Attorney, Agent, or Firm*—Trask, Britt

[57] ABSTRACT

The invention provides novel uses for n-glycolylated gangliosides and N-acetylated gangliosides, or derivatives and/or oligosaccharides thereof The invention further provides methods of obtaining such gangliosides, as well as vaccine compositions comprising said gangliosides. The gangliosides may be coupled to carriers and may be accompanied by adjuvants. The vaccine compositions can be used in the treatment of breast cancers, whereby the gangliosides are used to elicit an immune response to corresponding gangliosides on breast tumor cells.

22 Claims, No Drawings

OTHER PUBLICATIONS

Margalit et al., "Prediction of Immunodominant Helper T Cell Antigenic Sites From The Primary Sequence", *The Journal of Immunology*, vol. 138, pp. 2213–2229, No. 7, Apr. 1, 1987.

Marquina et al., "Gangliosides Expressed in Human Breast Cancer", *Cancer Research* 56, pp. 5165–5171, 1996.

Sonnino et al., "Recognition by Two–Dimensional Thin Layer Chromatography and Densitometric Quantification of Alkali–Labile Gangliosides from the Brain of Different Animals", *Analytical Biochemistry* 128, pp. 104–114, 1983.

Stroll et al., "Improved procedure for the construction of neoglycolipids having antigenic and lectin–binding activities, from reducing oligosaccharides", *Biochem. J.* 256, pp. 661–664, 1988.

Svennerholm, Lars, "Quantitative Estimation of Sialic Acids", *Biochem. Biophys. ACTA*, vol. 24, pp. 604–611, 1957.

Zopf et al., "Affinity Purification of Antibodies Using Oligosaccharide–Phenethylamine Derivatives Coupled to Sepharose", *Methods Enzymol.*, pp. 171–175, 1978.

VACCINE COMPOSITIONS FOR ELICITING AN IMMUNE RESPONSE AGAINST N-ACETYLATED GANGLIOSIDES AND THEIR USE FOR CANCER TREATMENT

CROSS-REFERENCE TO RELATED APPLICATIONS

This patent application is a continuation-in-part of U.S. patent application Ser. No. 08/365,684 filed on Dec. 29, 1994 (now U.S. Pat. No. 5,788,985 issued on Aug. 4, 1998), which claims priority from Cuban Patent Application No. 131/93 filed on Dec. 29, 1993. This patent application additionally claims priority from Cuban Patent Application No. 130/97 filed on Nov. 10, 1997.

FIELD OF THE INVENTION

The present invention relates to the field of active specific immunotherapy of cancer and among other things, provides vaccine compositions for producing or increasing the antibody immune response against gangliosides, especially N-glycolyl GM3 (NGcGM3) and N-acetyl GM3 (NAcGM3), which can be used for the prevention and treatment of cancer.

DESCRIPTION OF THE PRIOR ART

Gangliosides are glycosphingolipids that contain sialic acid and are expressed in all mammalian cell membranes. They comprise a saccharidic polar portion and a hydrophobic ceramide (e.g.,sphingosine and a long chain fatty acid). These compounds insert in the lipidic bi-layer that conforms the external cell membrane leaving the oligosaccharide chain exposed to the external surroundings.

Ganglioside expression varies in the different cell differentiation stages and growth fashions. The differentiation or undifferentiation that occurs during the oncogenic transformation is associated with the changes that occur in the distribution of the gangliosides. Moreover, the expression of certain gangliosides in mammalian tissues is species restricted. These gangliosides (called heterophiles) contains N glycolyl fleuraminic acid and are present in most species (mice, rats, dogs, horses, pigs, etc.) except humans and chickens. This "non self" characteristic of the N-glycolylated gangliosides has a very important incidence in the immunogenicity of these compounds in humans. This fact was indirectly observed in the 1920's by Hanganatzxu and Deicher (H-D), during a time when treatment of certain diseases with horse serum was common practice. Patients undergoing this treatment developed a disease called "serum sickness." It was shown that their serum reacted with components of the horse antiserum ("H-D antigens"), as well as erythrocytes of different species.

Later, these H-D antigens were extracted as horse erythrocyte gangliosides and their main epitope was defined as NgcNA$^\alpha$ (2$\rightarrow$3) Gal$\beta$ (1$\rightarrow$4) Glc (1$\rightarrow$R). Experiments performed with cultured human tumor cells and H-D antigens demonstrated the presence of these antigens in a group of human tumors. Thus, a tumor specific antigen seemed to have been found. Later, cell culture experiments using a bovine serum-free medium and the determination of the presence of lipid bound NGcNA in ganglioside extracts of tumor biopsies done by Gas Chromatography-Mass Spectrometry techniques showed that the levels of N-glycolylated gangliosides in the tumors studied was below 0.05% of the total sialic acid (Furukawa et al., 263 J. Biol. Chem. 18507 (1988)).

From the above results derived the present consensus that the N-glycolylated gangliosides have no practical value as targets for tumor immunotherapy. Nevertheless, more recently it has been shown that breast cancer, where N-glycolylated gangliosides are present in relatively large amounts, seems to be an exception to this rule. (Cuban Patent Application No. 131/93; Marquina et al., 56 Cancer Res. 5165–5171 (1996)). On the other hand, tumor associated gangliosides have been used as targets in treatment approaches, mainly in treatment of neuroectodermic-derived tumors (Gangliosides and Cancer Ed. H. F. Oettgen, p. 7 (1989)).

Immunization protocols with GM2 ganglioside absorbed to BCG have been performed in patients with melanoma. The presence of anti-GM2 antibodies of IgM and IgG isotypes was found in these patients. Patients with higher titers showed a more delayed relapse of 15 months (Livingston et al., 49 Cancer Res. 7045–7050 (1989)). Moreover, preliminary clinical trials in patients with melanoma have been performed. Immunizations with mixtures of gangliosides obtained from primary tumor cells, alone or included in liposomes, showed low antibody titers, mainly of IgG isotype, against gangliosides GM3, GD3, GM2 and 9-O-Acetyl GD3. This antibody response was short lasting and could not be maintained or increased by repetitive immunizations. Nevertheless, the patients with immune response showed, once more, a statistically significant delayed relapse (Portoukalain et al., 49 Int. J. Cancer 833–999 (1989)).

In an attempt to improve the immune response against gangliosides, clinical trials with melanoma patients using protein-GM2 ganglioside conjugates, particularly KLH-GM2, have started. Results obtained until now indicate higher production of IgM antibody titers and the presence of specific IgG antibodies with effector qualities, although the immune response is not yet a typical T-dependent response (Livingston, Proceedings of the Conference "Specific Immunotherapy of Cancer with Vaccines," The N.Y. Academy of Science; abst. 24 (1993); Livingston Immunol. Rev. 145, 147–166 (1995)).

Recent experiments on the immunogenicity in mice, using GD3 coupled by hydrophobic bonds to other vehicles, such as OMPC ("outer membrane protein complex") of *Neisseria meningitidis,* did not succeed in improving the quality of the antibody response against gangliosides. Livingston et al., 11 Vaccine 1199–1204 (1993)). These authors stressed that probably the characteristic of the "self" antigen of GD3 was the main cause hindering an IgG immune response.

Based on these and other experimental observations, there seems to exist some agreement in the field of ganglioside cancer vaccines that the two main problems to overcome for improving the immunogenicity of gangliosides are the variable degree of immunological tolerance, which exists with gangliosides in proportion to their expression on normal tissues, and the P cell independent character of these carbohydrate antigens. Therefore, selection as targets of gangliosides that are least expressed on normal tissues and the use of conjugated vaccines containing gangliosides covalently attached to immunogenic carrier proteins are currently being suggested. Livingston, 145 Immunol. Rev. 147–166 (1995)).

On the other hand, given the advantage of the immunogenicity of an heterophile antigen and its expression in breast tumors, N- glycolylated ganglioside based therapeutic vaccines can be effective in the treatment of human breast cancer.

Identification of a suitable antigen source is important for vaccine development. However, no natural source with this characteristic for NGcGM3 and NAcGM3 gangliosides has been described. As an alternative, total synthesis of N-glycolylated ganglioside derivatives has been proposed (U.S. Pat. No. 4,950,750 to Ogawa et al.). This alternative has the limitation that, as an antigen source for vaccines, the antibodies obtained against ganglioside derivatives generally do not recognize the original gangliosides. The use of monoclonal antibodies as protein carriers in conjugated vaccines has little precedence in general, and none in cancer therapeutic vaccines. Nevertheless, their use as carriers offers the advantages of immunotargeting and activation of the host's immune system.

SUMMARY OF THE INVENTION

This invention relates to vaccine compositions for stimulating or increasing the immune antibody response to N-glycolylated and N-acetylated gangliosides containing an effective amount of a pure N-glycolylated ganglioside, mainly NGcGM3 and/or a derivative thereof and/or its corresponding oligosaccharide, coupled through hydrophobic or covalent bonds to an appropriate vehicle and containing an adjuvant that can be of natural origin or a monoclonal antibody (mAb).

This invention also relates to the use of a vaccine composition for the treatment of cancer, the vaccine composition containing an effective amount of a pure N-acetylated ganglioside, mainly NAcGM3, and/or a derivative thereof, and/or its corresponding oligosaccharide, coupled through hydrophobic or covalent bonds to an appropriate vehicle and containing an adjuvant that can be of natural origin or a monoclonal antibody (mAb). The present invention teaches how IgG antibody specific responses against N-acetyl GM3, the most abundant ganglioside in normal tissues, can be consistently induced by immunization with OMPC-NAcGM3 hydrophobic complexes that are combined with a selection of adjuvants. The present invention also teaches how this vaccination procedures improves the resistance of mice to NAcGM3 expressing tumor challenges.

The invention also relates to the use of the hybridoma biomass used for the industrial production of monoclonal antibodies as a suitable biological source of gangliosides.

Another aspect of the invention lies in obtaining the glycolylated and acetylated gangliosides from the hybridoina biomass resulting from the industrial production of mAbs. Particularly NGcGM3 and NAcGM3, antigens both present in breast tumors, can be obtained in this way. These gangliosides, and/or a derivatives thereof, and/or their corresponding oligosaccharides are coupled to an adequate vehicle by hydrophobic binding, or to carrier proteins, mainly mAbs, by covalent binding. The invention additionally includes a method of augmenting an immune response in an animal comprising administering a vaccine composition comprising an immunogen selected from the group of immunogens consisting at N-glycolylated gangliosides or N-acetylated gangliosides, the corresponding oligosaccharides thereof, and mixtures thereof, coupled to a carrier protein and an adjuvant.

This invention further provides a method for treating cancer in a subject afflicted with cancer comprising administering to the subject a vaccine composition comprising an immunogen selected from the group of N-acetylated gangliosides, the corresponding oligosaccharides thereof, and mixtures thereof, coupled to a carrier protein and an adjuvant, particularly NAcGM3.

DETAILED DESCRIPTION OF THE INVENTION

I. Obtaining Gangliosides from the Hybridoma Biomass

A modification of Hakomori's method (Hakomori et al., Methods in Enzymology, Vol. 32, Part B, 350 (1974)) was used to process the hybridoma biomass obtained from production of mAbs in fermentors. The biomass (0.5–1 kg.) obtained by filtration of culture medium was homogenized with 2–5 L of methanol. An additional 2–5 L of methanol were then added before extraction under reflux for 5 to 20 hrs. The extract was filtered while hot and the transparent liquid obtained was left to stand 48 hours between $-20°$ C. and $-70°$ C. The precipitate was recovered by centrifugation at $4°$ C. and submitted to medium alkaline treatment (0.2 N NaOH—MeOH at $37°$ C. for between 1 and 7 hours). The precipitate was then neutralized with HCl—MeOH (0.2 N) and concentrated to dryness at a temperature below about $40°$ C.

The precipitate was then desalted by extensive dialysis at $4°$ C. with a carbonate buffer (pH 7) and then dried by lyophilization. The monosialoganglioside fraction was obtained by ionic exchange chromatography in DEAE Sephadex A 25 (Pharmacia, Sweden) Ac form (matrix volume/sample used: 1 ml DEAE Sephadex/0.1–1 mmol of NANA), eluting with 0.02 M NaAc in MeOH. After desalting, the fraction is dried by lyophilization.

Purification of the gangliosides GM3 and NGcGM3 was performed by adsorption chromatography with silicagel 60 (230–400 mesh, Merck, Germany). A column, containing to 40 g of silicagel, was equilibrated and eluted with $CCl_3H$/$MeOH$/$NH_3$ 2.5 M (v/v) 65:25:4. The fractions that contain GM3 and NGcGM3 alone, were mixed and dried.

Column monitoring was performed by HPTLC using 10×20 cm silicagel 60 plates (Merck, Germany) with a solvent system of $CCl_3H$/$MeOH$/$NH_3$ 2.5 M in 0.25% KCL(50:40:10) and stained with resorcinol reagent (Svennerholm L., 24 Biochem. Biophys. Acta 604–611 (1957)).

Quantification of gangliosides was also performed by the resorcinol method. Quantities between 20–60 mg of GM3 and NGcGM3 were obtained.

II. Construction of Vaccine Immunogens

As antigens for the immunogen preparations, any of the following can be used: N-glycolylated or N-acetylated gangliosides present in the tumors; oligosaccharides thereof, adequately modified in their reducing terminal by different spacers that improve their access to different components of the immune system; or derivatives of these gangliosides, modified by the incorporation of functional groups in the ceramide (e.g., amino, carboxyl or aldehyde groups), that allow covalent binding to carrier proteins.

As carrier proteins, any physiologically tolerated protein can be used. These should bear free amino and carboxyl groups that allow the covalent conjugation to the aforementioned antigens using any routine conjugation method (such as, for example, SPDP, carbodiimides, reductive amination, etc.). Murine monoclonal antibodies or the outer membrane proteins of different bacterias, such as *Neissaria meningitidis,* can be adequate carrier proteins. For those proteins with known primary amino acid sequences, some of the mathematical algorithms described for predicting helper T-cell epitopes can be used for selecting the adequate conjugation method, thus avoiding the possible damage of these epitopes produced by the coupling of the antigens. One such algorithm used in the present invention is that described by Margalit et al., 138 J. Immunol. 2213–2219 (1987).

Natural gangliosides can be used as components of the proteosomes conformed by the protein complex of the outer membrane of N. meningitidis. Preparation of this type of immunogen requires the previous dispersion of the proteosomes of N. meningitidis using sodium deoxycholate (0.1–1%) or sodium dodecil sulfate (0.1–1%) or Brij 96 (0.1–1%).

Dispersion is performed in an ultrasonic bath for 10–30 minutes, adding afterwards a solution containing 5 to 20 times excess of the ganglioside (or the gangliosides should it be a multivalent vaccine). The resulting dispersion is again ultrasonicated for 5 to 20 minutes and is left at room temperature for about 30 minutes. Finally, the dispersion is dialyzed until there is an absence of detergent.

Another efficient way to make the hydrophobic conjugation of the garigliosides to the outer membrane protein complex of N. meningitidis consists of introducing the dispersion of the proteins into a solution containing 1 to 10 times excess of the ganglioside (or the gangliosides should it be a multivalent vaccine) and a mixture of sodium dodecil sulfate (0.1–1%) and sodium deoxycholate (0.1–1%), by gentle mixing overnight at 4° C. Finally, the resulting dispersion is dialyzed until there is an absence of detergent.

The most effective formulations of our immunogen preparations made according to these methods contained 1 to 5 ganglioside mass units per protein mass unit. The most effective ganglioside doses were those between 10–400 $\mu$g. In the construction of conjugated immunogens (antigens covalently bound to carrier proteins), either ganglioside oligosaccharides or structurally modified gangliosides can be used. When ganglioside oligosaccharides are used as antigens, a spacer arm should be added to increase distance, thus avoiding cripticity and making the antigens more available to the immune system. As spacer reagents, aliphatic compounds (3 to 10 carbon atoms) that contain one free amino group in one end and a carboxyl group or an amino group in the other end of the chain can be used.

The coupling of the saccharide to the spacer reagent can be performed by a reductive amination reaction (Stoll, M. S., et al., 256 Biochem. J. 661–664 (1988)), using sodium cianoborohydride as a reductive agent.

Typical reaction conditions are: oligosaccharide (5–25 mmol), spacer arm (250–1250 mmol), sodium cianoborohydride (5–25 mg), reaction temperature (40° C.–70° C.), and reaction time (24–72 hours). The aminated oligosaccharide thus obtained is then coupled to N-succinimidyl 3-(2-pyridyldithio)propionate (SPDP, Carlsson J., 173 Biochem. J. 723–737 (1978)), at 3–5 times molar excess relative to the oligosaccharide and at room temperature for 6–10 hours.

Next, it is necessary to couple the carrier protein to the SDPD using a 3–5 molar excess relative to the oligosaccharide in a reaction at room temperature and for 4–12 hours. The reduction of the SPDP-protein complex was performed by combining the complex with a 10–50 mM dithiothreitol solution at room temperature for 1–5 hours.

Finally, coupling between the aminated oligosaccharide-SPDP and the reduced protein-SPDP complex is performed in a reaction in which the sugar is used in a 2–5 molar excess relative to the number of free amino groups in the proteins. The reaction occurs at room temperature for about 24–72 hours. Under these conditions, approximately 10–100 moles of the oligosaccharide (or its equivalent in mass) are coupled to the carrier proteins.

Another way of constructing immunogens to be used in multivalent vaccines involve the two methods previously described: the formation of proteosomes in which one or more gangliosides are bound noncovalently and the covalent bonding of one oligosaccharide from a ganglioside to which a spacer arm has been coupled.

The vaccine compositions comprising the immunogens selected from the group of immunogens consisting of N-glycolylated gangliosides or N-acetylated gangliosides, the corresponding oligosaceharides, and mixtures thereof, coupled to a carrier protein and an adjuvant, has been tested in mice and in chickens and has been found to have improved immunogenic and antitumoral properties. The test procedures and results are given in the examples below.

The following examples are illustrative of the present invention:

EXAMPLE 1

Isolation of GM3 and NGcM3 from the hybridoma biomass

The hybridoma biomass obtained from production in fermentors of monoclonal antibody for $t_3$ (CIMAB S. A., Cuba) was processed using a modification of Hakomori's method (Hakomori et. al., Methods in Enzymology, Vol. 32, Part 6, 350 (1974))

The hybridoma biomass (500 g), obtained by filtration of the culture medium, was homogenized with methanol (2.5 L) using a homogenizer. More methanol was added (2.5 L) and extraction under reflux during ten hours was performed. The extract was filtered while hot and the transparent liquid obtained left to rest at −20° C. for 2 days.

The precipitate was recovered by centrifugation at 4° C. and submitted to medium alkaline treatment (0.2 N NaOH/MeOH, 37° C., 2 h). After neutralizing with HCl (0.2 N), the precipitate was dried in a rotoevaporator and the solid was desalted by extensive dialysis at 4° C. against carbonate buffer pH 7. The dialyzed product was freeze dried.

The monosialoganglioside fraction was obtained by ionic exchange chromatography in DEAE Sephadex A-25 (Ac) eluting with NaAc 0.02 M in MeOH. After desalting by dialysis, this fraction was lyophilized, redissolved in $CCl_3H$/MeOH 4:1 (v/v) and applied to a 35 grams silicagel 60 column.

The column was eluted with a mixture of $CCl_3H$/MeOH/$NH_3$ 2.5 N (65:25:4), obtaining the corresponding gangliosidic fractions. The fractions containing GM3 and NGcM3 alone were mixed and dried using a rotoevaporator.

The determination of ganglioside contents in the different fractions of the silicagel separation was performed by high performance thin layer chromatography (HPTLC) in silicagel 60 plates with $CCl_3H$/NeOH/$NH_3$ 2.5 N in KCl 0.25% (50:40:10) solvent system and stained with resorcinol.

Yields of 30 mg of GM3 and 24 mg of NGcGM3 were obtained.

EXAMPLE 2

Obtainment of an immunogon based on non covalent coupling of the ganglioside NGcGK3 to the outer membrane protein complex (OMPC) of *N. meningitidis* by ultrasonication and dialysis The OMPC of *N. meningitidis,* provided by the Carlos J. Finlay Institute (C. Campa, et al., EP 301992), were used. 10 mg of the OMPC were dispersed for 10 minutes in a 0.3% solution of sodium deoxycholate in an ultrasonic bath. Then, a solution containing 20 mg of NGcGM3 ganglioside was added.

The resulting dispersion was again submitted to ultrasonic radiation for 5 minutes, leaving it to rest afterwards for 30 minutes. The separation of the soluble complex OMPC-NGcGM3 from the detergent was performed by dialysis, during 5 days, using a 100 kDa membrane. The grade of incorporation of the ganglioside to the protein was determined using the Bio-Rad reagent for the proteins and resorcinol for the sialic acid.

An incorporation of 2 mg of NGcGM3 per mg of OMPC was obtained.

EXAMPLE 3

Obtainment of an immunogen based on non-covalent coupling of the ganglioside NAcGM3 to the outer membrane protein complex (OMPC) of N. meningitidis by overnight mixing and dialysis

The OMPC of N. meningitidis, provided by the Carlos J. Finlay Institute (C. Campa, et al., EP 301992), were used. 10 mg of the OMPC were dispersed in a solution of 0.5% sodium deoxycholate and 0.1% sodium dodecyl sulfate, additionally containing 10 mg of NAcGM3, by gentle mixing overnight at 4° C. The separation of the soluble complex OMPC-NGcGM3 from the detergents was performed by dialysis, during 14 days, using a 3.5 kDa membrane.

The dialysate was ultracentrifugated at 100,000 g for one hour and the immunogen, present in the supernatant, was filter sterilized. The grade of incorporation of the ganglioside to the protein was determined using the Bio-Rad reagent for the proteins and resorcinol for the sialic acid.

An incorporation of 1 mg of NGcGM3 per mg of OMPC was obtained.

EXAMPLE 4

Obtaining of the immunogen (neoglycoproteins) based on the covalent binding of the oligosaccharide component of the NGcGM3 ganglioside to the P3 murine mAb a) Isolation of the oligosaccharide component of $NGcGM_3$ ($NGcGM_3OS$)

10 mg of NGcGM3 were dissolved in 4 mL of MeOH with the aid of an ultrasonicator and treated with ozone (Wiegandt H. and Baschang G. Z, Naturforsch., 20b:164–166, 1965) during 10 minutes. The solution was evaporated to dryness and the residue dispersed in 10 mL of $Na_2CO_3$ 0.1 M by stirring overnight, neutralized with DOWEX 50W-X8 and filtered through a sintered glass funnel. The resulting solution was extracted with $HCCl_3$ and the aqueous phase was studied by HPTLC to determine the completion of the reaction. The presence of oligosaccharide was verified by a positive resorcinol stain in the application point.

The final purification of NGcGM3OS was performed in a Sephadex G-25 column using HAc 0.1 M for elution. The structure of NGcGM3OS was finally determined by H1 Nuclear Magnetic Resonance and mass spectrometry (FAB spectrum).

b) Reductive amination of $NGcGM_3OS$

10 μmol of NGcGM3OS were dissolved in 5 mL of methanol containing 500 mmol of 1–8 diamine3, 6-dioxocctane, purged with argon and left to react for 2 hours at 50° C., after which 1 mg of $NaH_3CN$ were added and the reaction continued for 40 hours at 50° C. The reaction mixture was dried under argon and AcH added to eliminate the excess of $NaBH_3CN$. The modified oligosaccharide was desalted in a Biogel P-2 column and purified in a CM-cellulose column (Zopf et.al., 50 Methods Enzymol. 171–175, 1978).

The identification of the aminated derivative was performed by HPTLC, using silicagel 60 plates in pyridine-ethyl acetate-acetic acid-water (6:3:1:3) or chloroform-methanol-0.2% calcium chloride (60:35:8) solvents and detected with orcinol or resorcinol reagents.

c) Reaction of the aminated NGcGM3OS with the coupling reagent N-succinimidyl 3-(2-pyridyldithio) propionate (SPDP)

10 μmol of the oligosaccharide were dissolved in phosphate buffer solution 100 mM, NaCl 0.1 M, pH 7.5, then 30–50 mmol of SPDP was added and left to react during 6 hours at room temperature. The derivative obtained was purified using a Biogel P2 column. The identification of the derivative obtained was performed by HPTLC, using the same plates, solvents and detection systems as in step b.

d) Reaction of the monoclonal antibody P3 with SPDP 10 mg of the P3 monoclonal antibody, an IgM mAb that recognizes with high specificity N-glycolyl neuraminic acid bound to lipids, deposited at ECACC under no. 94113026, was dissolved at room temperature in phosphate buffer solution 100 nM, NaCl 0.1 M, pH 7.5. To this solution was added 5 mg of SPDP and the reaction left to continue for 8 hours. The separation of P3-SPDP was performed in a Sephadex G-50 column, using for elution a phosphate buffer solution 0.1 M, pH 6, 5 mM EDTA. The fractions containing the proteins were mixed and used for the following step.

e) Reduction of P3-SPDP derivative with dithiothreitol

To reduce the newly generated disulfide bridges, a 25 mM dithiothreitol solution in phosphate buffer solution 0.1 M, pH 6, 5 mM EDTA was added and allowed to react at room temperature for 2 hours. The derivative obtained was separated in a Sephadex G-50 column, using for elution the same solution referred to above.

The calculation of the number of SPDP moles coupled to P3 was estimated by calculating the free thiopyridine formed during the coupling process and is based on the measuring in an spectrophotometer of the extinction increase at the wave length of 343 nm and the application of the Lambert-Beer law. A molar extinction coefficient for thiopyridine of $7.06 \times 10^{-9} \times M^{-1} \times cm^{-1}$ was used.

f) Carbohydrate coupling to protein

The carbohydrate derivative obtained in step c was allowed to react during 48 hours with the protein obtained in step e. The neoglycoprotein obtained was separated from the reaction products using a Sephadex G-50 column. The estimation of the amount of carbohydrate coupled to the protein was determined by calculating the sialic acid content using the resorcinol reagent for the carbohydrate and Bio-Rad reagent for the protein. moles of NGcGM3OS per mol of P3 were obtained in these conditions.

The carbohydrate coupling to protein was also studied by electrophoresis in polyacrylamide gel (SDS-PAGE) under non reducing conditions followed by Western blot and reaction with anti-ganglioside specific mAbs.

EXAMPLE 5

Obtainment of the immunogen (Neoglycoproteins) by using the OMPC of the N. meningitidis, previously solubilized with the ganglioside NGcGM3 and then covalently coupled to NGcGM3OS a) Solubilization of the OMPC Solubilization of the OMPC was performed according to Example 2 or 3.

b) Coupling of NGcGM3OS to the OMPC-NGcGM3 soluble complex.

The oligosaccharide NGcGM3OS was obtained as described in step a of Example 4, submitted to reductive amination as in step b of Example 4 and coupled to SPDP as described in step c of Example 4. In parallel, the soluble protein complex OMPC-NGcGM3 was coupled to the SPDP reagent as described in step d of Example 4, reduced with dithiothreitol, as described in step e of Example 4 and finally coupled to the appropriate carbohydrate as described in step f of Example 4. In all, cases the amount of reagents and reaction conditions were those specified in Example 4. The analytical methods used for the characterization of the different $NGcGM_3$ derivatives, as well as those used for the characterization of the OMPC and its derivatives, were the same as those described in Example 4. An incorporation degree of 1 mg of NGcGM3OS per mg of OMPC proteosomes was obtained.

EXAMPLE 6

Immunological properties of vaccine compositions. Immunization of chickens

The different variants of the vaccine composition described above were used to immunize chickens and study the specific humoral immune response obtained. A group of chickens immunized weekly during one month with 1 mg NGcGM3 in 0.6 mL of PBS using Freund's complete adjuvant were used as a reference. Two weeks after the 4$^{th}$ dose a booster was applied and four days later the animals were bled. The same immunization protocol was used for the groups of chickens treated with each vaccine preparation.

The antibody response was evaluated by ELISA and TLC-immunostaining, using the ganglioside NGcGM3 as antigen. In all the groups of chickens immunized with the vaccine preparations, an increase in the levels of specific antibodies against NGcGM3 gangliosides with respect to the preimmune serum was evidenced. The control group also showed an increase in antibody response but of the IgM type, while all the vaccine preparations consistently showed a specific IgG response in most of the animals immunized.

EXAMPLE 7
Immunological properties of vaccine compositions. Immunization of mice In atypical experiment 10 C57BL/6 female mice were immunized with 4 doses (120 μg each, days 0,14,28 and 42) of the NAcGM3/OMPC immunogen, prepared according to Example 3, using intramuscular injection and with MONTANIDE ISA 51 (Freund's Incomplete Adjuvant (Seppic, Paris, France) as adjuvant.

The sera were collected the day before the first injection (preimmune) and then 2 weeks after the final immunization (day 56) for measuring antibody response. The presence of specific IgG antibodies vs. NAcGM3 was measured by ELISA and TLC-immunostaining. In the sera of 7/10 animals, the presence of IgG antibodies were detected after the immunization procedure, while in the pre-immune sera of these mice antibodies against gangliosides were absent. In TLC-immunostaining experiments, the sera reacted with NAcGM3 and didn't react with NGcGM3, GM2, NGcGM2, GM1, GD1a, GD1b, GD3 and GT1b.

EXAMPLE 8
Antitumor immunity induced by vaccine compositions

In a typical antitumoral experiment, 10 C57BL/6 female mice were immunized with 4 doses (120 μg each, days 0,14,28 and 42) of the NAcGM3/OMPC immunogen, prepared according to Example 3, using intramuscular injection and with Freund's complete adjuvant and Montanide ISA 51 (Seppic, Paris, France) as adjuvant. As a control, another group of 10 mice, inoculated with PBS instead the vaccine, were used in the experiment. On day 21, mice were challenge by subcutaneous injection of B16 murine melanoma cells ($10^3$) whose viability had been confirmed by dye exclusion. The mice were observed for 100 days and the size of external tumors developing at the inoculation site were measured twice a week.

TABLE I

Growth of B16 melanoma tumor and survival in C57BL/6 mice after immunization with the vaccine.

| | Number of Mice survived | | Tumor Volume (cm³) by day 32 |
|---|---|---|---|
| Immunizations | day 50 | day 100 | Median value. (mice tested) |
| PBS | 2 | 1 | 2.46 (7) |
| NacGM3 Vaccine | 8 | 8 | 0 (8) |

EXAMPLE 9
Gangliosides expressed in breast tumors

Biopsies of ten breast tumors were obtained during surgery. Samples were hystologically classified and stored at −70° C. until use. Tumors were processed individually following the method briefly described below:

To wet and weighed tumors were added 2 volumes of distilled water and homogenized in cold (4° C.). Total protein contents was determined in a sample of the homogenate by the Lowry method. To the remaining volume of each sample was added 5 volumes of a mixture of $CCl_3HI$—$CH_3OH$ (2:1) and stirred during 1 hour at 37° C. Then $CH_3OH$ was added to adjust the ratio of $CCl_3H$:$CH_3OH$ to 1:1 and the extraction procedure repeated. The final mixture was centrifuged, separating the supernatant. Precipitate was again extracted by stirring at 37° C. during 2 hours with a mixture of $CCl_3H$:$CH_3OH$:$H_2O$ (1:2:0.8). It was again centrifuged separating supernatant.

Both supernatants were mixed and concentrated to dryness obtaining the mixture of total lipids of each tumor. The mixtures of total lipids, dissolved in 5 mL of $CCl_3H$:$CH_3OH$ (9:1), were applied to Phenyl Sepharose columns (2 mL) and washed with 3 volumes of the same solvent mixture followed by $CCl_3H$:$CH_3OH$ (85:15). Gangliosides were eluted afterwards with 5 volumes of $CCl_3H$:$CH_3OH$ (1:1) and 5 volumes of $CH_3OH$ The individual samples of the tumor ganglioside mixtures were studied by HPTLC and 2d-HPTLC by the method of Sonnino et.al. (128 Anal. Biochem. 104–114 (1983)). The relative amounts of the main gangliosides were estimated by densitometry.

The results obtained indicate that the main gangliosides in breast tumors are $GM_3$ (average: 356.4 ng/mg protein) and $GD_3$ (average: 133.1 ng/mg protein) followed by $GD_{1a}$ and $GT_{1b}$. The expression of $GM_3$ and $GD_3$ in normal breast tissue is as an average (183.5 and 48.6 ng/mg protein respectively) lower than in breast tumors.

For the characterization of the minor breast tumor gangliosides a pool with a mass of 83 grams was also studied. This tumor mass was processed and extracted, as previously described.

The total mixture of gangliosides was submitted to ionic exchange chromatography in DEAE Toyopearl and the total acid fraction submitted again to chromatography in a Q-Sepharose column with a gradient system from which 9 fractions were obtained. The chromatographic studies in 2d-HPTLC, combined with FAB-MS and the TLC immunostaining experiments with a monoclonal antibody specific to O-acetylated gangliosides, allowed the detection of the presence of $OAcGD_3$ and $OAcGT_3$ in the sample studied.

It was also possible to detect, in the ganglioside mixtures of breast tumor, the presence of bands with identical Rf than NGcGM3. The TLC immunostaining study with antibodies that react with H-D antigens showed, additionally, the presence of 2 other glycolylated gangliosides.

TLC immunostaining studies were performed both with H-D and the anti-OAc ganglioside mAbs for the mixture of gangliosides obtained from 10 individual tumors. Results are shown in Table II.

TABLE II

Presence of H-D antigens in the total ganglioside fraction isolated from human tumors

| METHOD | | SAMPLE | | | | | | |
|---|---|---|---|---|---|---|---|---|
| | | 3705 (b) | 3735 | 3782 | 3820 | 3931 | 3464 | 3806 |
| NgcGM3 (c) | Immunostaining (a) | + | + | + | + | ++++ | + | − |
| U1 (NGNA) (d) | Immunostaining (a) | − | + | ++ | − | ++ | ++ | − |
| U2 (NGNA) (d) | Immunostaining (a) | − | − | − | − | − | − | − |

TABLE II-continued

Presence of H-D antigens in the total ganglioside fraction isolated from human tumors

| METHOD | SAMPLE | | | | | | |
|---|---|---|---|---|---|---|---|
| | 3705 (b) | 3735 | 3782 | 3820 | 3931 | 3464 | 3806 |

Notes:
(a) TLC-immunostaining with H-D antibody.
(b) 3705, 3735, 3782, etc, are ind±vidualhuman breast tumor samples.
(c) NGNA: N glycolyl neuraminic acid
(d) U1 and U2: unknown N glycolylated gangliosides
(e) +, low reactivity; +++, middle ractivity; ++++, strong reactivity; −, r The relative amounts of the different types of lipid-bound sialic acids in breast cancer were studied in 4 tumors.

For this purpose, the mixture of individual gangliosides were submitted to methanolysis in 0.5% HCl/MeOH at 100° C. for 2 hours. Samples were dried under $N_2$ atmosphere and 0.5 mg of phenyl-a-N-acetylglucosaminide was added as an internal standard. Samples were then acetylated in a mixture of acetic anhydride:pyridine (1:1) at 100° C. for 30 minutes.

After eliminating the excess of acetic anhydride by evaporation with MeOH, the samples were dissolved in $CCl_3H$ and were submitted to GC/MS in a Jeol DX-304 equipment with an OV-17 column (0.25 mm×5 m) using the electronic impact mode. The temperature of the column was 228° C. and of the injector was 260° C. The carrier gas used was He at 0.5 mL/min. Results are shown in Table III.

TABLE III

Analysis of sialic acid species (Composition)

| Sample No.[a] | | NANA[b] | NGNA[b] | O-Ac NANA[b] |
|---|---|---|---|---|
| 3849 | GC/MS | 75.11%[c] | 16.60% | 8.20% |
| 3464 | GC/MS | 89.20% | 5.82% | 4.89% |
| 3931 | GC/MS | 76.55% | 11.55% | 11.89% |
| 3806 | GC/MS | 88.56% | | 11.44% |

Notes:
[a] 3849, 3464, 3931, 3806 are individual tumor samples (see table II).
[b] NANA:N acetyl neuraminic acid, NGNA:N glycolyl neuraminic acid, O-Ac NANA: O acetyl N acetyl neuraminic acid.
[c] Values are percent of total lipid bound sialic acid.

What is claimed is:

1. A vaccine composition for stimulating or increasing the antibody immune response against N-acetylated gangliosides comprising
    an immunogen selected from the group of immunogens consisting of N-acetylated gangliosides, the corresponding oligosaccharide, and mixtures thereof;
    a carrier protein comprising the outer membrane protein complex (OMPC) of *Neisseria meningitidis*, wherein said immunogen is coupled to said carrier protein by non-covalent hydrophobic interaction; and
    an adjuvant.

2. The vaccine composition of claim 1 wherein the effective amount of the immunogen used is an amount between 10 and 400 µg.

3. The vaccine composition of claim 1 wherein the immunogen comprises a soluble complex of the corresponding N-acetylated ganglioside and the OMPC of *N. meningitidis* and wherein said immunogen is coupled by a non-covalent bond to the corresponding ganglioside oligosaccharide through a spacer arm.

4. The vaccine composition of claim 3 wherein the spacer arm is a saturated or unsaturated diamine containing 3–10 carbon atoms.

5. The vaccine composition of claim 1 wherein the carrier protein comprises a monoclonal antibody.

6. The vaccine composition of claim 5 wherein the monoclonal antibody is coupled by a covalent bond to the corresponding N-acetylated ganglioside oligosaccharide through a spacer arm.

7. The vaccine composition of claim 6 wherein the spacer arm is a saturated or unsaturated diamine containing 3–10 carbon atoms.

8. The vaccine composition of claim 1 wherein the adjuvant is Freund's Incomplete Adjuvent.

9. The vaccine composition of claim 1 wherein the vaccine composition further comprises an immunogen selected from the group of immunogens consisting of the purified GD3 ganglioside and the corresponding oligosaccharide.

10. The vaccine composition of claim 1 wherein said N-acetylated ganglioside is N-acetyl GM3 (NAcGM3).

11. The vaccine composition of claim 10 wherein the N-acetylated ganglioside GM3 is purified from a biological source.

12. The vaccine composition of claim 10 wherein the biological source from which the N-acetylated ganglioside is purified is a hybridoma biomass used in the production of a monoclonal antibody.

13. A method of stimulating or increasing the immune response against N-acetylated gangliosides in a subject comprising the administration to said animal an immunogen selected from the group of immunogens consisting of N-acetylated gangliosides, the corresponding oligosaccharide, and mixtures thereof, coupled to a carrier protein comprising the OMPC of *Neisseria meningitidis* by non-covalent hydrophobic interaction and to an adjuvant.

14. The method of claim 13 wherein the effective amount of the immunogen administered to a subject is an amount between 10 and 400 µg.

15. The method of claim 13 wherein the immunogen comprises a soluble complex of the corresponding N-acetylated ganglioside and the OMPC of *N. meningitidis* and wherein said immunogen is coupled by a non-covalent bond to the corresponding ganglioside oligosaccharide through a spacer arm.

16. The method of claim 15 wherein the spacer arm is a saturated or unsaturated diamine containing 3–10 carbon atoms.

17. The method of claim 13 wherein the carrier protein comprises a monoclonal antibody.

18. The method of claim 17 wherein the monoclonal antibody is coupled by a covalent bond to the corresponding N-acetylated ganglioside oligosaccharide through a spacer arm.

19. The method of claim 18 wherein the spacer arm is a saturated or unsaturated diamine containing 3–10 carbon atoms.

20. The method of claim 13 wherein the adjuvant used is Freund's Incomplete Adjuvant.

21. The method of claim 13 wherein the vaccine composition further comprises an immunogen selected from the group of immunogens consisting of the purified GD3 ganglioside and the corresponding oligosaccharide.

22. The method of claim 13 wherein said N-acetylated ganglioside is N-acetyl GM3 (NAcGM3).

* * * * *

UNITED STATES PATENT AND TRADEMARK OFFICE
CERTIFICATE OF CORRECTION

PATENT NO.     : 6,149,921
DATED          : November 21, 2000
INVENTOR(S)    : Rolando Perez Rodriguez et al.

It is certified that error appears in the above-identified patent and that said Letters Patent is hereby corrected as shown below:

Title page,
Item [30], Foreign Application Priority Data, insert -- Dec. 29, 1993 [CU] Cuba………….131/93 --
Item [56], References Cited, OTHER PUBLICATIONS, "Furukawa et al." reference, change "Tissue" to -- Tissues --; change "Hamiltion" to -- Hamilton --;
"Stroll et al." reference, change "Stroll" to -- Stoll --

Assistant Examiner, change "Zemar" to -- Zeman --
Item [57], ABSTRACT,
Line 3, after "thereof" insert -- . --

Column 1,
Line 20, after "and" insert -- , --

Column 3,
Line 40, change "procedures" to -- procedure --
Line 48, after "Particularly" and "antigens" insert -- , -- and after "NAcGM3" delete ","
Line 50, change "derivatives" to -- derivative --
Line 51, after "oligosaccharides" insert -- , --

Column 4,
Line 29, after "containing" insert -- 10 --

Column 5,
Line 16, change "garigliosides" to -- gangliosides --

Column 6,
Line 2, change "oligosaceharides" to -- oligosaccharides --
Line 48, change "immunogon" to -- immunogen -- and change "non covalent" to -- non-covalent --

UNITED STATES PATENT AND TRADEMARK OFFICE
CERTIFICATE OF CORRECTION

PATENT NO. : 6,149,921
DATED : November 21, 2000
INVENTOR(S) : Rolando Perez Rodriguez et al.

It is certified that error appears in the above-identified patent and that said Letters Patent is hereby corrected as shown below:

Column 7,
Line 23, after "(NGcGM$_3$OS)" insert -- . --
Line 41, after "NGcGM$_3$OS" insert -- . --
Line 45, change "1 mg" to -- 10 mg -- and change "NaH$_3$CN" to -- NaBH$_3$CN --
Line 59, after "(SPDP)" insert -- . --
Line 67, after "SPDP" insert -- . --

Column 8,
Line 8, after "dithiothreitol" insert -- . --
Line 18, change "an" to -- a --
Line 22, after "protein" insert -- . --
Line 30, change "protein. moles" to -- protein. 25 moles --
Line 54, after "all" delete "," and after "cases" insert -- , --

Column 9,
Line 3, after "dose" insert -- , --
Line 18, change "atypical" to -- a typical -- and after after "experiment" insert -- , --
Line 22, change "Adjuvant" to -- Adjuvant) --
Line 25, change "(preimmune)" to -- (pre-immune) --
Line 29, change "were" to -- was --
Line 31, after "mice" insert -- , --
Line 43, after "instead" insert -- of --
Lines 44-45, change "challenge" to -- challenged --

Column 10,
Line 3, change "contents" to -- content --
Lines 11-12, after "centrifuged" insert -- , -- and after "separating" insert -- the --
Line 20, after "CH$_3$OH" insert -- . --
Lines 31-32, after "gangliosides" insert -- , --

UNITED STATES PATENT AND TRADEMARK OFFICE
CERTIFICATE OF CORRECTION

PATENT NO.    : 6,149,921
DATED         : November 21, 2000
INVENTOR(S)   : Rolando Perez Rodriguez et al.

It is certified that error appears in the above-identified patent and that said Letters Patent is hereby corrected as shown below:

Column 11,
Line 13, (third line under Table II), change "ind±vidualhuman" to
-- individual human --
Line 15, (6th Line under Table II), change "ractivity;" to -- reactivity; --
Line 48, after "comprising" insert -- : --
Line 50, change "the" to -- a --
Line 52, change "the" to -- an --
Line 57, after "wherein" change "the" to -- an --

Column 12,
Line 14, change "Adjuvent" to -- Adjuvant --
Line 25, change "claim 10" to -- claim 11 --
Line 31, after "comprising" delete "the" and change "said animal" to -- the subject --
Line 33, change "the" to -- a --
Line 35, after "comprising" change "the" to -- an --
Line 37, after "wherein" change "the" to -- an --
Line 38, change "a subject" to -- the subject --
Lines 60-61, change "vaccine composition" to -- immunogen --

Signed and Sealed this

Eighth Day of July, 2003

JAMES E. ROGAN
*Director of the United States Patent and Trademark Office*